United States Patent
Singer

(10) Patent No.: US 10,874,573 B1
(45) Date of Patent: Dec. 29, 2020

(54) NON-TRAUMATIC, NON-OCCLUSIVE EXTREMITY SUPPORT SYSTEM

(71) Applicant: Adam Joel Singer, Bell Canyon, CA (US)

(72) Inventor: Adam Joel Singer, Bell Canyon, CA (US)

(73) Assignee: SINGER INNOVATIONS, LLC, Bell Canyon, CA (US)

( * ) Notice: Subject to any disclaimer, the term of this patent is extended or adjusted under 35 U.S.C. 154(b) by 298 days.

(21) Appl. No.: 16/139,089

(22) Filed: Sep. 23, 2018

(51) Int. Cl.
  *A61G 13/12* (2006.01)
  *A61G 7/075* (2006.01)
  *A61F 5/37* (2006.01)

(52) U.S. Cl.
  CPC .......... *A61G 13/128* (2013.01); *A61F 5/3769* (2013.01); *A61G 7/075* (2013.01); *A61G 13/121* (2013.01); *A61G 13/1235* (2013.01); *A61G 2200/322* (2013.01); *A61G 2200/325* (2013.01); *A61G 2200/327* (2013.01)

(58) Field of Classification Search
  CPC .... A61G 13/128; A61G 7/075; A61G 7/0755; A61G 13/121; A61G 13/1235; A61G 2200/322; A61G 2200/325; A61G 2200/327; A61G 13/124; A61G 13/1245; A61F 5/3769; A47C 20/023; A47C 20/022; A47C 20/021
  See application file for complete search history.

(56) References Cited

U.S. PATENT DOCUMENTS

| 2,237,252 | A | * | 4/1941 | Longfellow | ........... A61G 7/075 602/20 |
|---|---|---|---|---|---|
| 2,801,142 | A | | 7/1957 | Adams | |
| 2,998,008 | A | | 8/1961 | Klesa | |
| 3,297,026 | A | | 1/1967 | van Pelt | |
| 3,528,413 | A | | 9/1970 | Aydt | |
| 3,931,654 | A | | 1/1976 | Spann | |
| 3,939,829 | A | | 2/1976 | Spann | |

(Continued)

OTHER PUBLICATIONS

Mizuho Medical Co., LTD Hongo Shintoku Building 7F, 3-38-1, Hongo, Bunkyo-ku, Tokyo, 113-0033, Japan Operating Table Accessories Catalogue http://www.mizuhomedical.co.jp/products/up_img/1459217527-914781.pdf.

(Continued)

*Primary Examiner* — Nicholas F Polito
*Assistant Examiner* — George Sun

(57) ABSTRACT

An extremity support system comprising a board having an upper surface that supports a resilient member. The board has a curved portion that facilitates it to pivot when connected to a table or bed. It also has a plurality of openings for holding a plurality of straps that can be positioned over the resilient member. The resilient member also includes a rounded end for facilitating the board to pivot; and a top furrow that supports and provides access to an extremity extending off the surface of the table or bed of a patient laying in a plurality of positions. In addition, the straps have methods of placement to function as non-occlusive non-obstructive guardrails that maintain the extremity in the furrow of the resilient member, do not interfere with the ability of the board to pivot, and do not touch the extremity under usual circumstances thereby preventing injuries to an arm or a leg.

17 Claims, 13 Drawing Sheets

(56) References Cited

U.S. PATENT DOCUMENTS

| | | | | |
|---|---|---|---|---|
| 4,210,317 | A * | 7/1980 | Spann | A61G 13/12 482/142 |
| 4,414,969 | A | 11/1983 | Heyman | |
| 5,149,033 | A | 9/1992 | Burzler | |
| D359,190 | S | 6/1995 | Hargest | |
| 5,477,866 | A | 12/1995 | Davenport | |
| D382,057 | S | 8/1997 | Swedberg | |
| 5,725,486 | A | 3/1998 | Engelman | |
| 5,745,939 | A | 5/1998 | Flick | |
| 6,065,166 | A | 5/2000 | Sharrock | |
| 6,067,678 | A * | 5/2000 | Trevino | A61G 1/00 5/628 |
| 6,490,742 | B2 | 12/2002 | Hall | |
| 6,622,727 | B2 | 9/2003 | Perry | |
| 6,823,870 | B1 | 11/2004 | Hill | |
| 7,017,215 | B1 * | 3/2006 | Singer | A47C 20/023 5/646 |
| D518,894 | S | 4/2006 | Kim | |
| 7,634,828 | B2 * | 12/2009 | Elhabashy | A61G 13/12 5/621 |
| 7,640,610 | B2 | 1/2010 | Mervar | |
| 7,849,540 | B2 | 12/2010 | Hill | |
| D642,280 | S | 7/2011 | Goumas | |
| 3,043,241 | A1 | 10/2011 | Goumas | |
| 8,286,285 | B2 | 10/2012 | Mahler | |
| 8,418,696 | B2 * | 4/2013 | Marasco | A61G 13/124 128/877 |
| 8,602,032 | B2 | 12/2013 | Goldsmith | |
| D736,391 | S | 8/2015 | Johnson | |
| 9,265,681 | B1 * | 2/2016 | Bell | A61G 5/122 |
| 9,301,868 | B2 | 4/2016 | Castle | |
| D759,825 | S | 6/2016 | Johnson | |
| D783,834 | S | 4/2017 | Johnson | |
| D805,206 | S | 12/2017 | Hill | |
| 2003/0145862 | A1 * | 8/2003 | Perry | A61G 7/065 128/845 |
| 2010/0305431 | A1 * | 12/2010 | Crisco | A61G 13/1235 600/424 |
| 2012/0247483 | A1 * | 10/2012 | Flynn | A61G 13/0036 128/845 |
| 2013/0037036 | A1 * | 2/2013 | Carlin | A61G 13/124 128/845 |
| 2014/0238408 | A1 * | 8/2014 | Shepherd | A61G 13/101 128/845 |
| 2017/0112655 | A1 | 4/2017 | Giap | |
| 2017/0196724 | A1 | 7/2017 | Wilson | |
| 2018/0344556 | A1 * | 12/2018 | Garman | A61G 5/1091 |

OTHER PUBLICATIONS

Allen Medical Systems, Inc., 100 Discovery Way, Acton, MA 01720, U.S.A. Product Catalog http:www.allenmedical.com/resources/catalog-and-brochures.

Steris Corporation, 5960 Heisley Road, Mentor, OH 44060 U.S.A. Product Catalog http://www.steris.com/healthcare/products/surgical-table-accessories/leg-supports/.

Steris Corporation, 5960 Heisley Road, Mentor, OH 44060 U.S.A. Product Catalog http://www.steris.com/healthcare/products/surgical-table-accessories/arm-supports/.

* cited by examiner

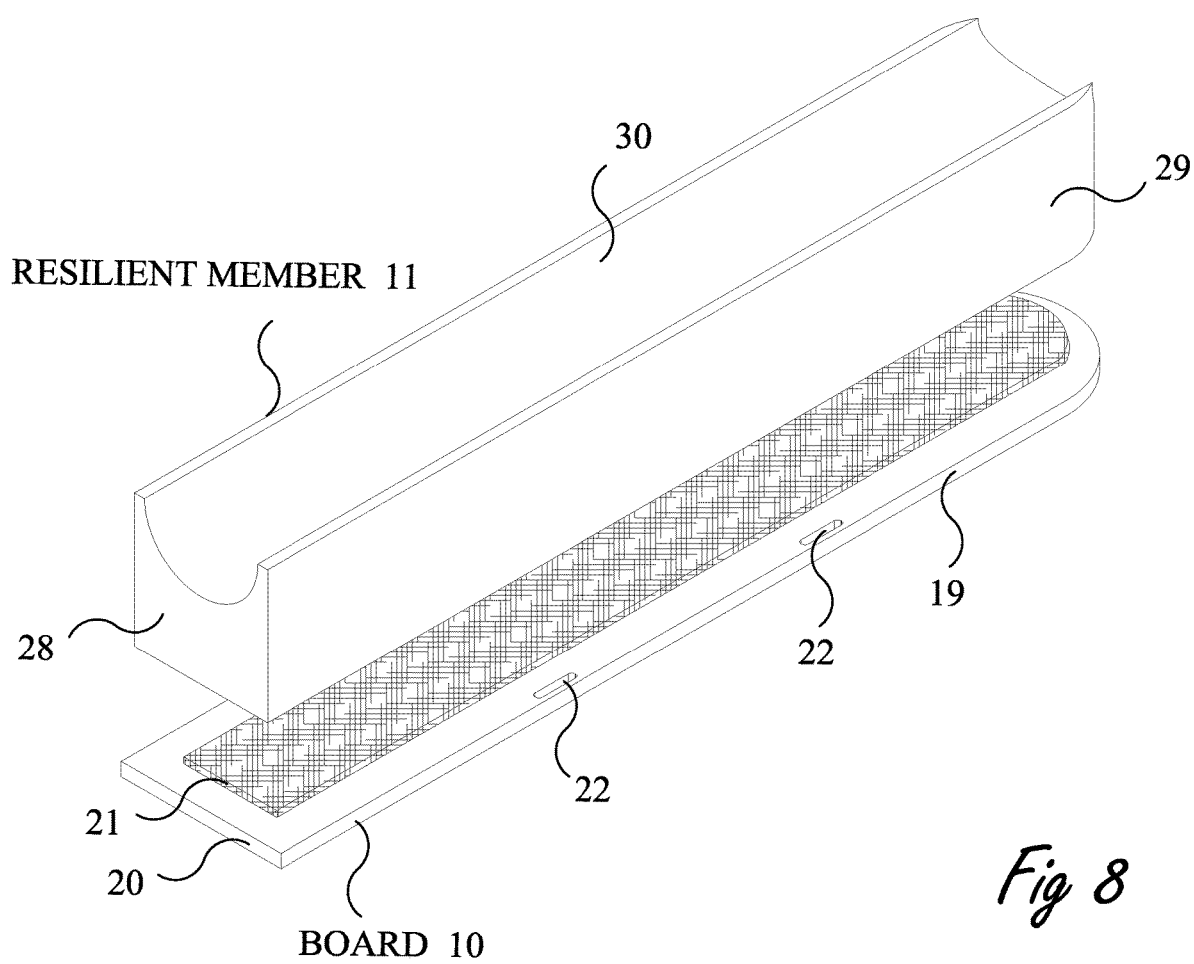

NON-TRAUMATIC, NON-OCCLUSIVE EXTREMITY SUPPORT SYSTEM

BACKGROUND—CROSS-REFERENCE TO RELATED APPLICATION

This patent claims priority of my Provisional Patent Application, Ser. No. 62/658,578, Filed Apr. 16, 2018.

BACKGROUND—PRIOR ART

Straps are ubiquitous in medical settings. When a procedure is to be done to a patient, it is the standard of care, well known to medical personnel, to place an extremity on a board that is attached to a table or bed and then wrap encircling straps in direct communication with the patient's extremity and the board to bind, restrain, immobilize, grip, grasp, or hold the extremity. For example, an arm is commonly restrained to the board during abdominal surgery or a leg is frequently restrained to the board during genitourinary surgery. It is also commonplace to bind the extremity to the board when operating on the arm or leg. Unfortunately, this creates and increases points of pressure (also known as pressure points) to the extremity in a multitude of positions. As a result, patients who undergo surgical and non-surgical procedures often sustain significant strap-induced injuries that involve, but are not limited to, neurological, vascular, lymphatic, joint, soft tissue, musculoskeletal, and cutaneous structures of the extremities. A multitude of patients are especially vulnerable to strap injuries, such as those who are elderly or have cancer, disabilities, disfigurements, burns, skin disorders, nutritional deficiencies, and immunologically compromised states. Also, the straps often occlude a multitude of vascular access lines, interfere with the function of a multitude of medical devices placed in and on the extremity, limit access to the extremity, and prevent safe movable adjustments of the extremity. Further, to the detriment of the patient, the straps can interfere with a mechanism on the undersurface of the board that functions to enable the board to pivot when attached to the table or bed. Even though placing straps in the manner described has an adverse impact on the quality of patient care, the health care community and the medical industry have not done enough to address the safety, quality, and ergonomic aspects of the straps and the extremity supports that are in use.

The prior art and products available in the marketplace are replete with extremity support devices for which straps may or not be used. However, each device has one or more significant disadvantages that include, but are not limited to the following:

(a) some devices support either the arm or the leg, but not both, and are therefore less cost-effective;
(b) some supports are disposable and thereby environmentally unfriendly and less cost-effective;
(c) some boards have firm padded surfaces (with or without cushions) that support the extremity, but apply substantial harmful pressure points to the extremity;
(d) some supports do not attach to the board, table, or bed and can become unsteady and fall over;
(e) some devices support only a portion of the extremity so that the unsupported portion of the extremity is vulnerable to injury;
(f) some devices only support the extremities of patients in a limited number of positions;
(g) some devices encase or enclose the extremity and thereby limit access to the extremity;
(h) some devices do not disclose methods to place straps thereby putting the extremity at high risk of significant injury from falling off the device;
(i) some devices have flat or contoured supportive surfaces and use straps to prevent the extremity from falling off the surface of the device, but are placed in a random or haphazard manner to restrain, bind, grip, grasp, hold, and/or immobilize the extremity that can apply potentially harmful injurious pressure points and damage structures of the extremity;
(j) some devices have flat or contoured supportive surfaces with straps that can slip out of position that can cause potential occlusion and obstructive forces that can further harm the extremity;
(k) some devices have flat or contoured supportive surfaces with straps that can limit access to the extremity, hinder movable adjustments of the extremity, obstruct intravascular lines, occlude bodily structures (e.g., veins, arteries, lymphatics), and interfere with the function of the multitude of medical devices placed in and on the extremity;
(l) some devices have flat or contoured supportive surfaces with straps that directly communicate and can interfere with the mechanism that allows the board to properly move and pivot; and
(m) some devices have flat or contoured supportive surfaces having extremity straps that restrain, bind, grip, grasp, hold, and/or immobilize the extremity that can apply potentially harmful injurious pressure points to the extremity; limit access to the extremity; hinder movable adjustments of the extremity; obstruct and occlude intravascular lines, vascular structures, and lymphatics of the extremity; interfere with the function of the multitude of medical devices placed in and on the extremity; and hinder pivoting of the board.

Furthermore, I have found that the prior art, insofar as I am aware, does not adequately protect and can potentially harm a fractured, disabled, or disfigured extremity as commonly found in disabled and special-needs patients, such as those having a history of breast cancer surgery and dialysis arm fistulas. For example, applying pressure to disfigured and fractured extremities can be harmful and create further disabilities. Also, pressure applied to arms of breast cancer patients who have had surgical removal of their axillary lymph nodes can obstruct extremity lymphatics and damage their arms. In addition, pressure on dialysis arm fistulas can be obstructive and clot off the vascular flow through the fistula.

I have found the following examples of prior-art arm boards and leg supports, but all such devices of which I am presently aware have significant disadvantages as noted above.

Prior-Art Patents

U.S. Pat. No. 3,931,654 to Spann (1976) describes a device for supporting a lower leg and foot of a patient while lying on their side wherein hook-and loop strip members placed thereover provide a pressure sensitive fastening means for adjusting the closure of a slot and a gripping force against the patient's foot.

U.S. Pat. No. D382,057 to Swedberg, et al. (1997) shows an ornamental design for a hand support cushion device without base attachments or safety straps wherein the device can topple over and the hand can fall off the cushion.

U.S. Pat. No. 7,634,828 to Elhabashy (2009) describes a surgical arm pillow for use with an operating table and an arm board for a patient lying in a lateral position wherein an adjustable strap extends across a top arm support channel for securing an arm in the channel without specifications to insure the strap does not apply pressure to the arm. Furthermore, a bottom adjustment strap extends both across a bottom arm channel and an underside of the arm board for the purpose of securing a surgical arm pillow that communicates and can interfere with a pivoting mechanism of the board.

U.S. Pat. No. 6,490,742 to Hall, et al. (2002) discloses a support for an appendage comprising a plurality of stackable bolsters in which mating surfaces are engaged and stabilized by frictional and lateral support between adjacent bolsters that, according to the disclosure, is "relatively stable even when used on a bed or examination table" that can topple over. Also, the appendage can fall off the support which has a parabolic indentation that can be made from materials from the group of firm foam material or rigid plastic or other polymeric material that can increase pressure points to the appendage.

U.S. Pat. No. 3,528,413 to Aydt (1970) describes an adjustable limb support wherein straps tightened around an injured arm holds the injured arm in place for either healing or medical treatment thereof that apply pressure points to the arm.

U.S. Pat. No. 2,801,142 to Adams (1957) discloses an adjustable limb support that attaches to an operating table wherein the support is a U-shaped adjustable limb rest that supports a small portion of the limb and does not have straps to secure the limb.

U.S. Pat. No. 7,640,610 to Mervar (2010) teaches a support for an arm wherein straps disperse pressure to retain the arm within a groove.

U.S. Pat. No. 4,210,317 to Spann, et al. (1980) describes a trough shaped apparatus for supporting and positioning a patient's arm and a shoulder in a prone position on an operating table for laminectomy. A cuff device for gripping the arm adjacent to the shoulder in such a manner that the shoulder is maintained in a desired rotated position applies pressure around the arm. In addition, the device does not have attachments that can stabilize the device to a table or an arm board.

U.S. Pat. No. 4,414,969 to Heyman (1983) discloses a device for restraining movements of a person's limb having a generally long rectangular flexible member which encircles the limb providing a means for continually adjusting both the degree of tightness of the restraint about the limb and a support structure that can cause pressure points and damage to the limb.

U.S. Pat. No. 5,149,033 to Burzler (1992) discloses a support apparatus to elevate one or both extremities having securement straps for fastening the apparatus to a supporting structure, but without specifications for straps to secure the extremities. Also, the support is made of rigid material such as wood, rigid plastic, or metal that can cause pressure points to the extremities although soft cushioning material may be used to line the depression.

U.S. Pat. No. 3,939,829 to Spann (1976) describes a restraining cuff and the like from a block of polyurethane foam so as to provide a closed circumferential layer of resilient deformable material around an extremity connected to a flat strap for fastening to a bed that can cause pressure points to the extremity.

U.S. Pat. No. 6,065,166 to Sharrock, et al. (2000) describes a pneumatic support cushion for a person's body in a lateral decubitus position wherein a set of mechanical fastening or restraining devices may be selectively engaged thereby restricting the configuration of the support cushion that can cause pressure points to the body and does not support an extremity.

U.S. Pat. No. 3,297,026 to van Pelt (1967) discloses a restraining device in which a foam pad is adapted to be wrapped around a body part being restrained and a free end of a strap is secured to a chair or bed or other support that can cause pressure points to an extremity.

U.S. Pat. No. 6,823,870 to Hill, et al. (2004) describes device for restraining a patient using straps against the patient that can cause pressure points to an extremity.

U.S. Pat. No. 2,998,008 to Klesa (1961) describes a restraining device to encircle a wrist or an ankle that can cause pressure points to the arms and legs.

U.S. Pat. No. 8,602,032 to Goldsmith (2013) describes a set of arm positioning sleeves that wrap and apply pressure around a portion of each arm of a patient lying on an operating table with a set of body straps that connect to each arm positioning sleeve and a set of operating table rails.

U.S. Pat. No. D359,190 to Hargest et al. (1995) show an ornamental design of a foot support cushion having an arcuate cradle area wherein the cushion can place pressure on the foot and does not have specifications for securement to a surface to prevent the cushion from falling over.

U.S. Pat. No. 8,043,241 (2011) and D642,280 (2011) to Goumas et al. disclose a device wherein one or more straps fix an arm in a cradle that immobilizes and restricts arm movement for recovery from shoulder surgery and straps are fashioned to make a sling that encircles a waist or neck of a patient that can cause pressure points to the arm.

U.S. Pat. No. 8,286,285 to Mahler (2012) describes an orthopedic support pillow wherein straps touch, restrain, elevate, and support an arm in a prone position that can cause pressure points to the arm.

U.S. Pat. No. 7,849,540 to Hill (2010) teaches a system of support cushions of different shapes and firmness for a person's torso, head, and feet wherein various mechanical fasteners such as hook and loop straps or the like located on covers can attach the system to the person that can cause pressure points.

U.S. Pat. No. D805,206 to Hill (2017) shows an ornamental design for an arm support device and US Pat. Nos. D736,391 (2015), D759,825 (2016), and D783,834 (2017) to Johnson et al. show an ornamental design for a leg support device each of which is without straps to secure either the arm or the leg and does not have means to prevent the devices from toppling over.

U.S. Pat. No. D518,894 to Kim (2006) shows an ornamental design for an arm support without straps to secure the arm.

U.S. Pat. No. 6,622,727 to Perry (2003) discloses a wedge pillow and an extended arm cushion that is used in conjunction with a hook-and-loop fastening strap to secure an arm and a cushion to an arm board wherein the strap comes in contact with the arm and a pivoting mechanism of the board that can cause pressure points to the arm and interfere with the arm board to pivot.

U.S. Pat. No. 8,418,696 to Marasco (2013) describes an arm board securement arrangement for securing a patient's arm to the arm board and a plurality of wrap members for gripping the arm.

U.S. Pat. No. 5,725,486 to Engelman (1998) discloses an orthotic leg elevator to cradle a leg with detachable straps that bind the leg at spaced positions.

U.S. Pat. No. 5,745,939 to Flick et al. (1998) teaches a pair of troughs that support, but restrain and restrict movement of a patient's legs that can cause pressure points to the legs.

U.S. Pat. No. 5,477,866 to Davenport (1995) describes a support pillow constructed to prevent sideward or rotational movement of a leg and foot that can cause pressure points to the leg and foot.

U.S. Pat. No. 9,301,868 to Castle (2016) discloses a leg support pillow wherein the depth is configured to maintain a person's feet in an upright orientation and a foot drop strap that bears against a bottom portion of the feet preventing the feet from dropping forward that applies pressure points to the foot.

US Published Pat. App. No. 2017/0196724 to Wilson (2017) discloses a device having a pair of wings that apply pressure to a patient's arms to maintain position of the arms above their head.

US Published Pat. App. No. 2017/0112655 to Giap (2017) describes substrates which are wrapped around a patient's arms that can hinder access to the arms. Giap further teaches straps that can apply pressure points and harm the arms as well as obstruct and occlude a multitude of medical devices placed in and on the arms.

Non-Patent Literature

ALLEN MEDICAL SYSTEMS, INC., 100 Discovery Way, Acton, Mass. 01720, U.S.A. Product Catalog http://www.allenmedical.com/resources/catalog-and-brochures STERIS CORPORATION, 5960 Heisley Road, Mentor, Ohio 44060 U.S.A. Product Catalog http://www.steris.com/healthcare/products/surgical-table-accessories/leg-supports/_ http://www.steris.com/healthcare/products/surgical-table-accessories/arm-supports/MIZUHO MEDICAL CO., LTD Hongo Shintoku Building 7F, 3-38-1, Hongo, Bunkyo-ku, Tokyo, 113-0033, Japan Operating Table Accessories Catalogue http://www.mizuhomedical.co.jp/products/up_img/1459217527-914781.pdf Advantages Accordingly, several advantages of one or more aspects are to provide an extremity support structure assembly that attaches to an operating table, treatment table, or bed (afterword referred to as "the table") that overcomes the disadvantages of the prior art, including devices in the marketplace. It is an all-in-one device that can support an arm or a leg, has a soft cushioned supportive ergonomic resilient member that attaches securely to a board, supports an extremity in a multitude of patient positions on the table; has means for placing a plurality of straps safely in a methodological manner wherein straps do not slip out of position and are not used as occlusive or obstructive restraints, do not touch the extremity under usual circumstances, do not cause pressure points and/or injuries to the extremity, function to maintain the extremity on the support, provide access to the extremity, facilitate movable adjustments of the extremity, do not interfere with the access or function of a multitude of intravascular lines and a multitude of medical devices placed in and on the extremity, do not hinder pivoting of the board, and have methods and ergonomic specifications of design for non-traumatically supporting a fractured, disabled, and/or disfigured extremity as commonly found in a special needs patient as disclosed in the present invention.

Several specific advantages for one or more aspects are:

1. The extremity support system can be used to support either a right or a left arm or leg of a patient (human or animal), thereby cost-effectively replacing a multitude of other devices that support only the arm or the leg.

2. The components of the extremity support system can be constructed from recyclable disposal or reusable materials thereby being a cost-effective and environmentally responsible device.

3. The board is constructed from rigid radiolucent or radiopaque hard materials that can support the resilient member constructed of highly resilient foam rubber or other suitable viscoelastic cushioning with or without a soft fabric cover (removable or permanent). It may be manufactured through methods well known in the art. It has a furrow that comfortably, ergonomically, non-traumatically, securely, safely supports, provides access to, and softly buttresses the many pressure points of the extremity that extends off the surface of the table when the patient and the extremity support are stationary and during movable adjustments of the table, patient, extremity, resilient member, and extremity support system.

4. The board and the resilient member each have matching components of hook-and-loop fasteners for stabilizing the extremity support system.

5. The board can attach to any side or end of the table using a device well known by those skilled in the art that fastens to the undersurface of the board, whereby the extremity support system can lock in position, move, or pivot without hindrances and support the extremity ergonomically, comfortably, and safely in a multitude of patient positions such as sitting, kneeling, side lying, semi-side lying, lithotomy, jackknife, lateral, prone, and supine.

6. The board of the extremity support system has a plurality of openings for engaging a plurality of straps well known by those skilled in the art whereby straps do not communicate or interfere with attachment and pivoting mechanisms of the device fastened to the undersurface of the board.

7. The system is designed so that the straps can be positioned in a plurality of configurations that remain in position after being placed. The straps serve as guardrails (afterward referred to as "straps," "guardrails," or "guardrail straps") that prevent removal of the extremity from the resilient member and do not touch the extremity under usual circumstances to avoid pressure, occlusion, obstruction and/or trauma to the extremity, multitude of intravascular access lines, and/or the multitude of medical devices placed in and on the extremity, and therefore, straps are not used as restraints as described in prior art devices.

8. The system allows the plurality openings to engage the plurality of straps in the plurality of configurations to provide additional stability to the resilient member without straps touching the extremity and/or pivoting attachment device of the board.

9. The extremity support system provides methods for the plurality of openings to engage straps in the plurality of configurations for preventing the extremity from being removed from the resilient member.

10. The system supports the extremity wherein guardrail straps and resilient member prevent the extremity from falling out of the furrow and off the resilient member, enable movable non-traumatic adjustments of the extremity during repositioning of the extremity, patient, table, resilient member, board, and extremity support system.

11. The resilient member, with and without the use of guardrail straps, enables access and supports the extremity for placement, removal, maintenance, and troubleshooting the multitude of medical devices in the multitude of patient positions such as sitting, kneeling, side lying, semi-side lying, lithotomy, jackknife, lateral, prone, and supine.

12. The system has the advantages specified above when used for patients without disabilities and for patients with disabilities such as those with fractured extremities or disfigured extremities from strokes, cerebral palsy, traumatic injuries, neuromuscular disorders, and/or degenerative joint diseases, and for patients with special needs where minimizing pressure points to their extremities is essential such as in post-surgical breast cancer patients and in patients with fistulas in their arms used for hemodialysis.

13. The system redefines and repurposes the conventional teaching of using straps as physical restraints that can injure an extremity. Each strap is used as a safety guardrail feature that prevents the patient from removing their extremity from the support device and provides additional stabilization of the resilient member.

Further advantages of one or more or various aspects will become apparent from a consideration of the ensuing description and the accompanying drawings.

SUMMARY

A patient extremity support system comprises a resilient member that reversibly attaches on top of and is supported by a board or rigid support having a plurality of openings. The support attaches to an operating table, treatment table, or bed (afterward referred to as "the table") using an attachment device that is well known and that fastens to the undersurface of the board and allows the board to attach to the table and pivot. The resilient member has a furrow and a rounded end that supports a right or left extremity and enables pivoting of the board. The openings in the board can hold a plurality of straps that are well known by those skilled in the art. The straps can be placed in a plurality of configurations for providing additional stability to the resilient member; the straps and furrow of the resilient member function together to prevent the extremity from falling off or being removed from the resilient member and the straps function as guardrails that do not have physical contact (i.e., do not communicate) with the extremity under usual circumstances and do not communicate with the attachment device of the board. The extremity support system can be either reusable or disposable and attaches to any side or end of the table by conventional means. Numerous modifications and adaptations may be made without departing from the spirit and scope of the invention as disclosed in the embodiments.

DRAWINGS—FIGURES

FIG. 8 is another exploded perspective view of the resilient member and the board of FIG. 1.

Figure 1:
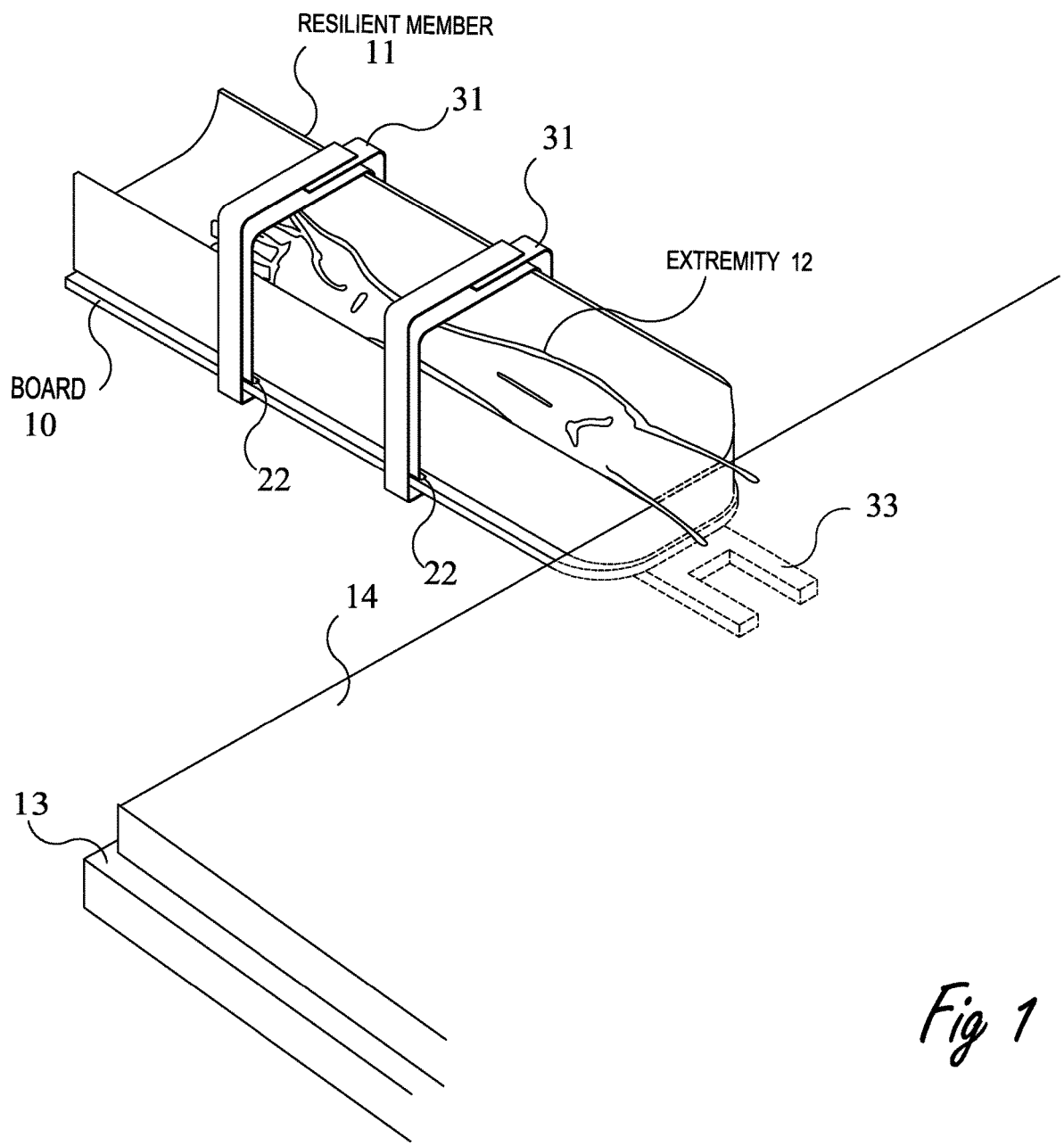
FIG. 1 is a perspective view an extremity on a resilient member and straps attached to a board connected to a table according to one preferred embodiment.

DRAWINGS—REFERENCE NUMERALS 10 board
11 resilient member
12 extremity
13 table
14 top cushion of table
15 undersurface
16 upper surface
17 curved portion
18 platform portion
19 opposite sides of board
20 outer end
21 band of hook-and-loop fasteners
22 opening
23 pivoting attachment device
24 bottom surface
25 stripe of hook-and-loop fasteners
26 top surface
27 rounded end
28 distal end
29 side of resilient member
30 furrow
31 straps of hook-and loop fasteners
32 end of strap
33 pivoting attachment component
34 rod
35 handle

DETAILED DESCRIPTION

First Embodiment—FIG. 1

Figure 11:
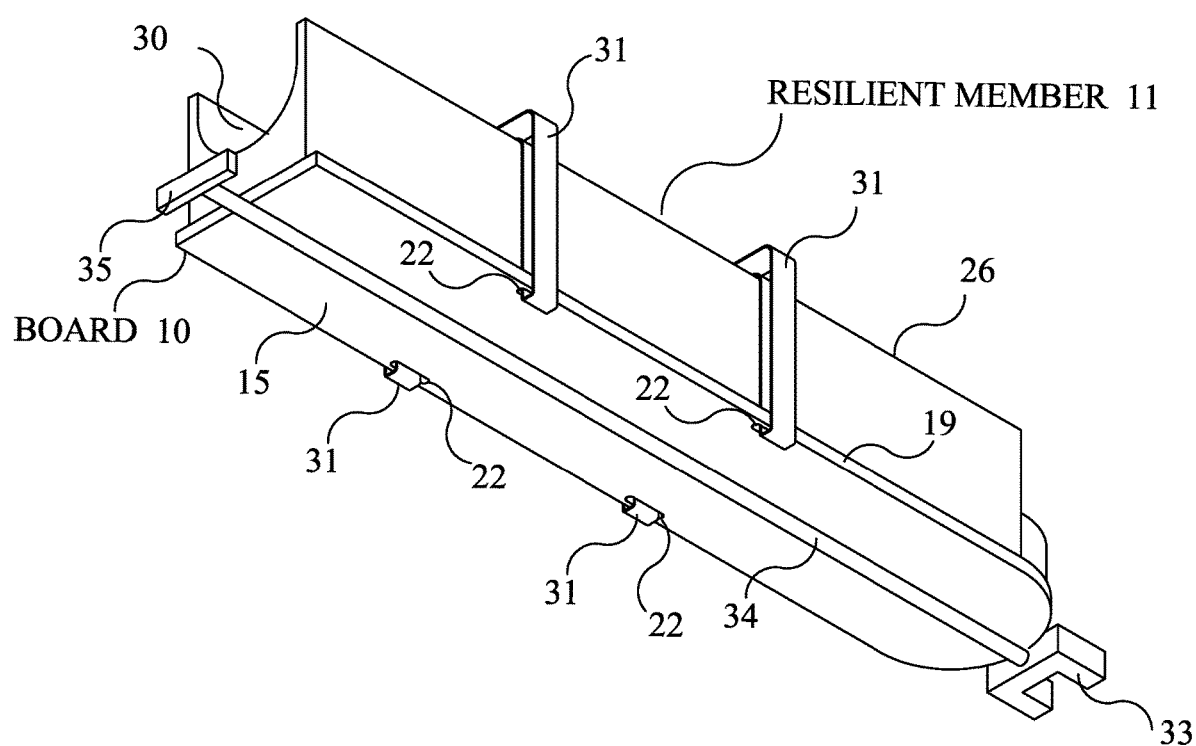
FIG. 11 is a perspective view of the board and resilient member of FIG. 1 with straps.
Figure 12:
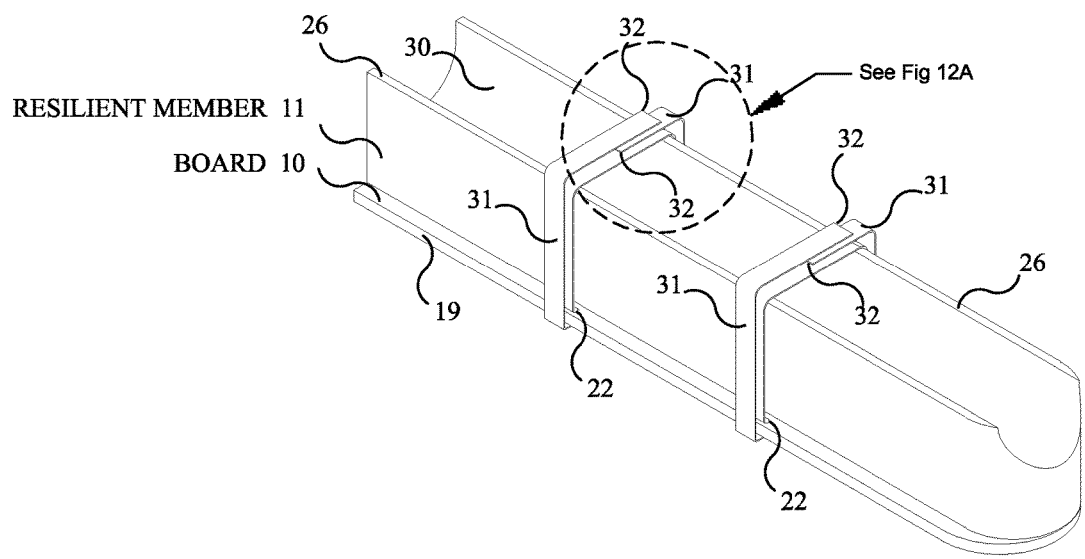
FIG. 12 is another perspective view of the board and resilient member of FIG. 1 with straps.
Figure 12A:
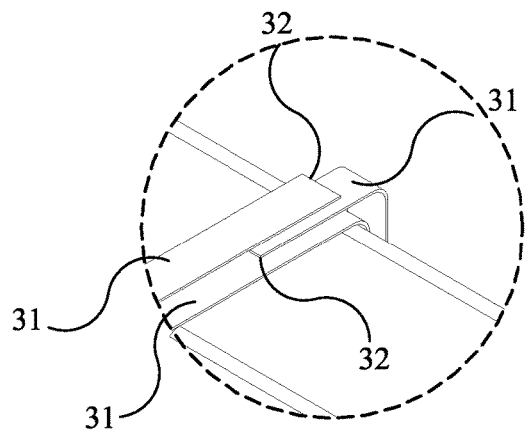
FIG. 12a is detailed perspective view of the straps of FIG. 12.

One embodiment of an extremity support system comprises (FIG. 1) a board 10 and a resilient member 11 for supporting a patient's extremity 12 off a table 13 having a top cushion 14. Board 10 is pivotally attached to a side or end of table 13 by a known pivoting attachment component 33 which is described in connection with FIG. 3. Openings 22 in board 10 hold straps 31, which are described in connection with FIGS. 11 and 12 so that straps 31 can span over resilient member 11 without touching extremity 12.

Description—First Embodiment—FIGS. 2-8

Figure 2:
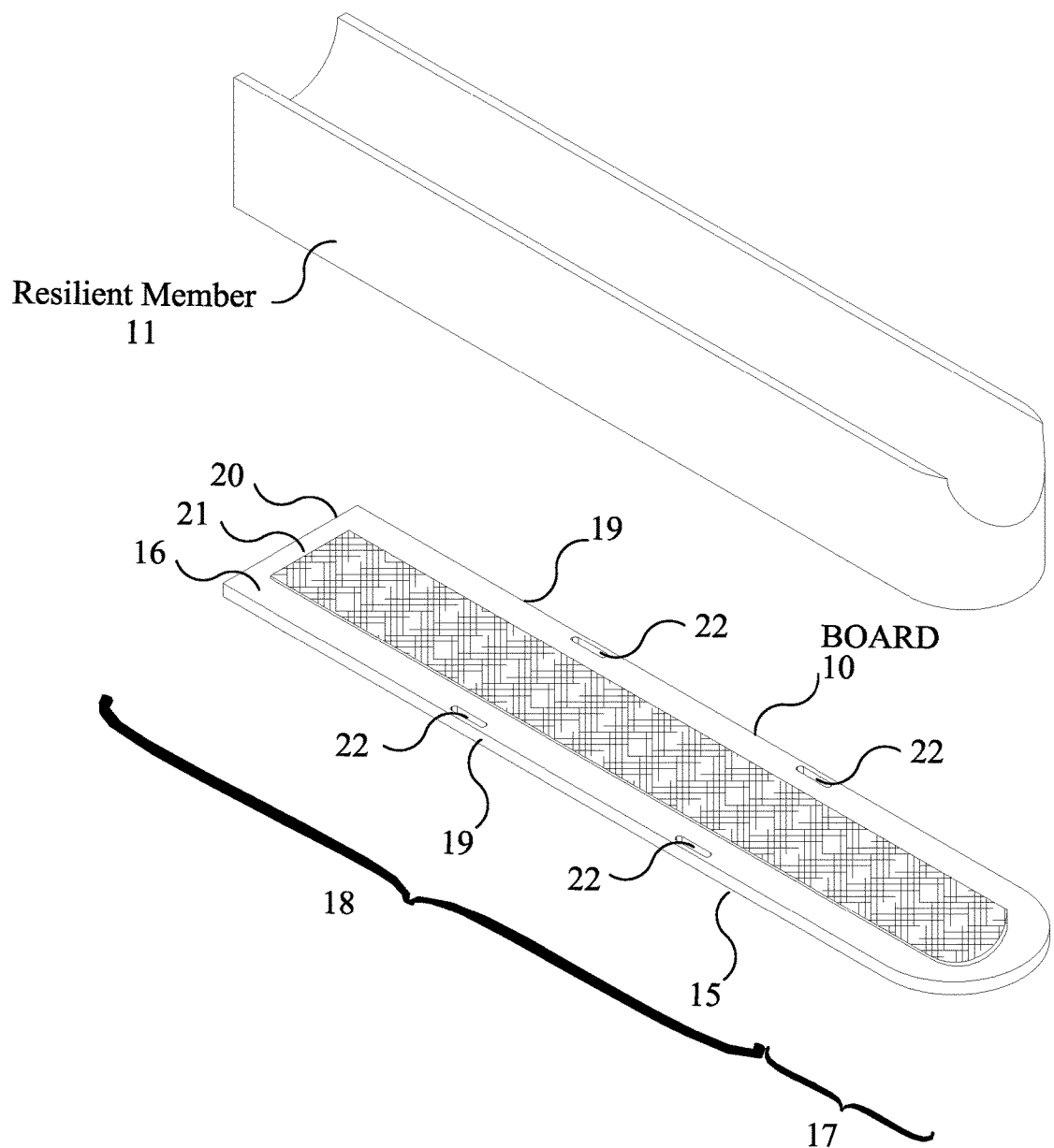
FIG. 2 is an exploded perspective view of the board and the resilient member of FIG. 1.

As shown in FIG. 2, board 10 is constructed of hard rigid material(s) for supporting resilient member 11. Board 10 has an undersurface 15 that is flat, an upper surface 16 that is flat, a curved portion 17 that is semicircular in shape, a platform portion 18 that is rectangular in shape and has a pair of opposite sides 19, and an outer end 20. Upper surface 16 has a longitudinal band of one component 21 of a hook-and-loop fastener and platform portion 18 has a pair of openings 22 (afterward also referred to as "strap openings" or "guardrail strap openings") near opposite sides 19. Each opening 22 is mirror image with respect to a line extending the length of the board 10 from curved portion 17 to outer end 20 and parallel to the opposite sides 19. Board 10 is radiolucent to facilitate taking x-ray images of extremity 12. In other embodiments, the degree of radiolucency and/or radiodensity of the board 10 can vary.

Figure 3:
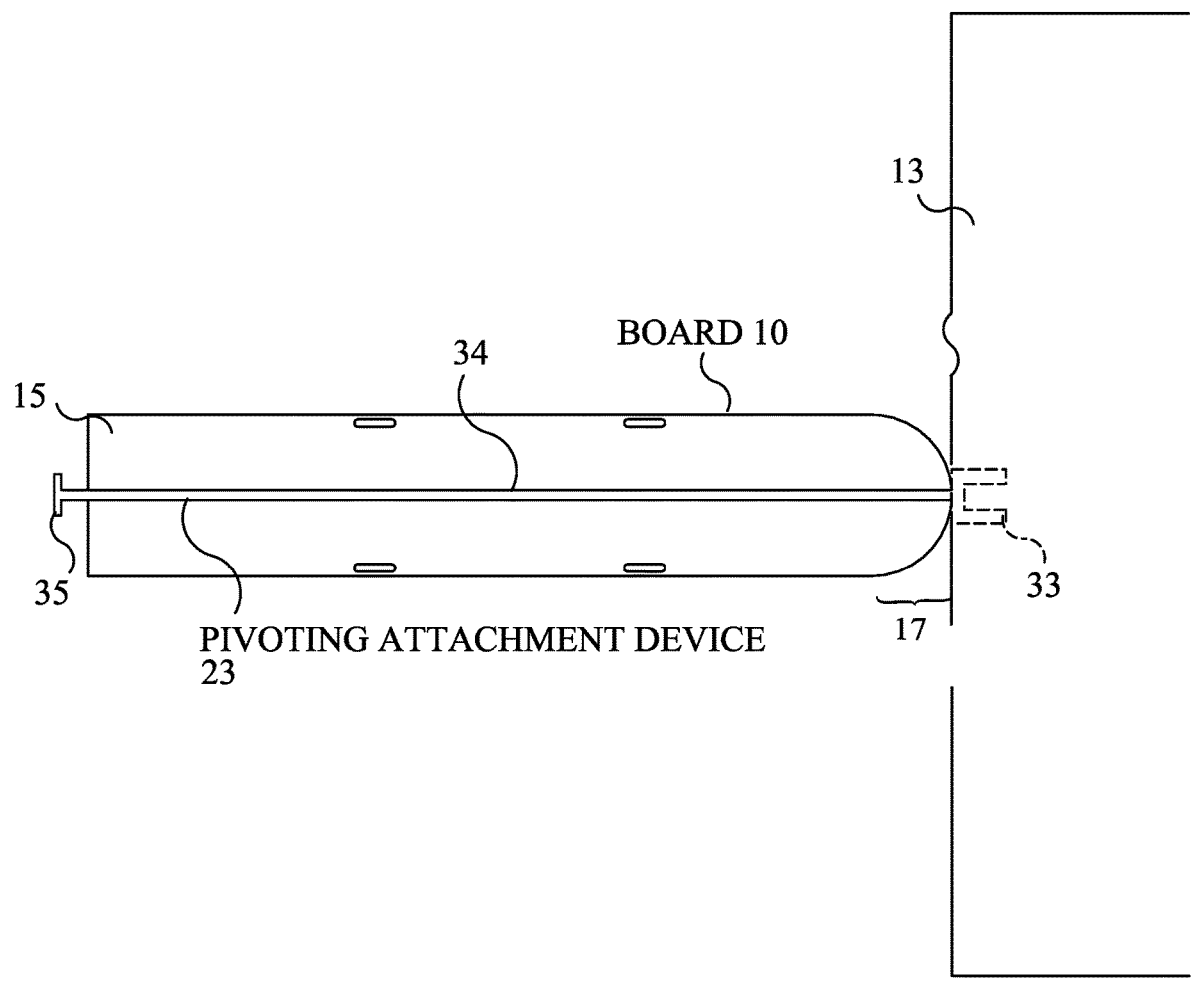
FIG. 3 is a perspective view of the bottom of the board attached to the table of FIG. 1.

As shown in FIG. 3, in the first embodiment, a pivoting attachment component 33 of a pivoting attachment device 23 (mechanism not shown but well known by those skilled in the art), is used to pivotally connect board 10 to table 13. Device 23 comprises component 33, a rod 34, an unlocking handle 35 and other components that are not shown. Device 23 attaches to undersurface 15 of board 10 (attachment hardware well known but not shown) so that component 33 is oriented toward curved portion 17 of board 10. Handle 35 is oriented toward outer end 20 of board 10. Component 33 attaches to any side or end of table 13 by methods well known to those skilled in the art so that curved portion 17 of board 10 is contiguous to table 13 and allows board 10 to pivot about table 13 in three-dimensional space. In other embodiments, board 10 and table 13 may not be contiguous as described in connection with FIG. 13. Device 23 holds board 10 locked when in a stationary position, but pivots when handle 35 unlocks component 33.

Figure 4:
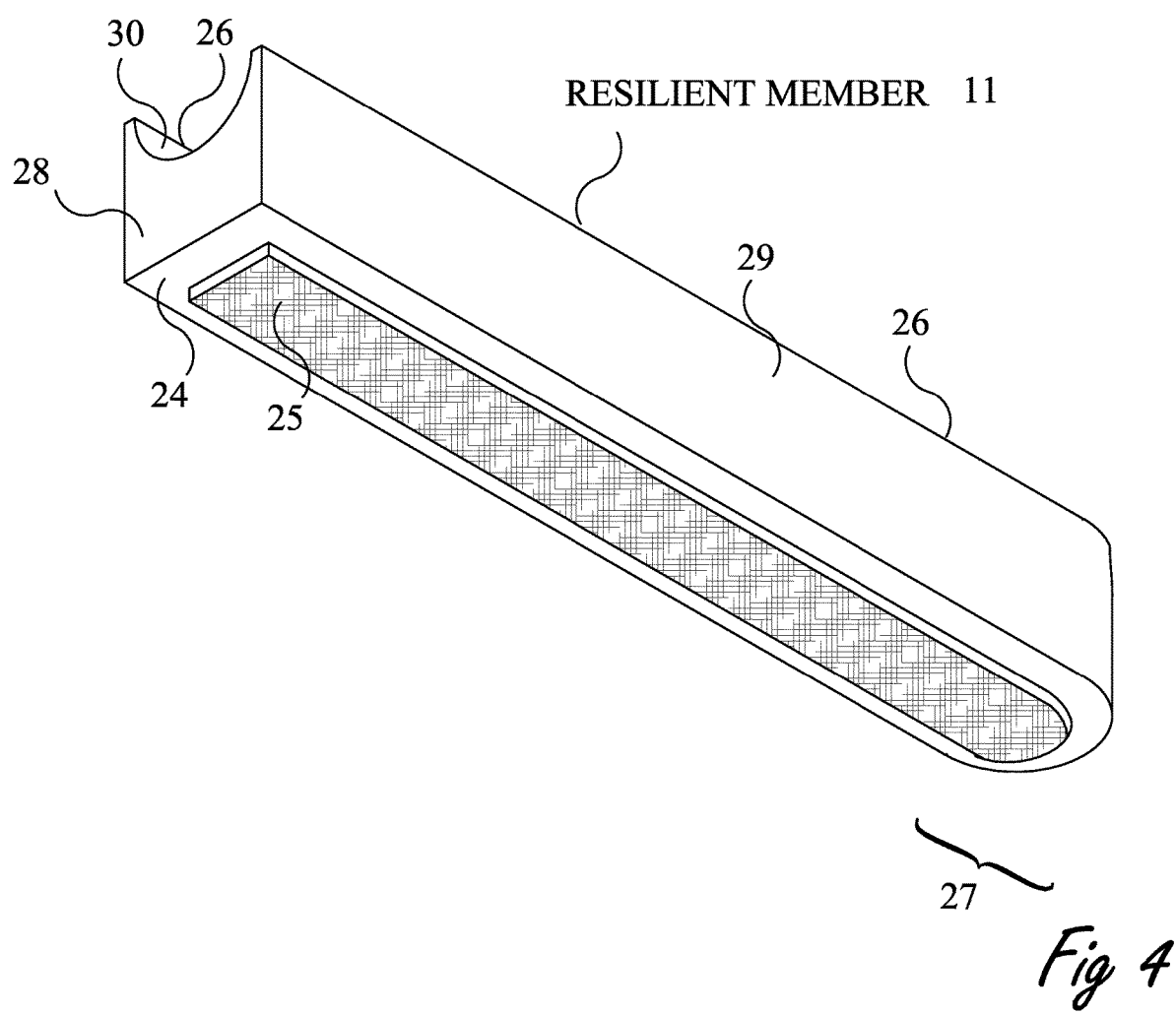
FIG. 4 is another perspective view of the resilient member of FIG. 1.
Figure 5:
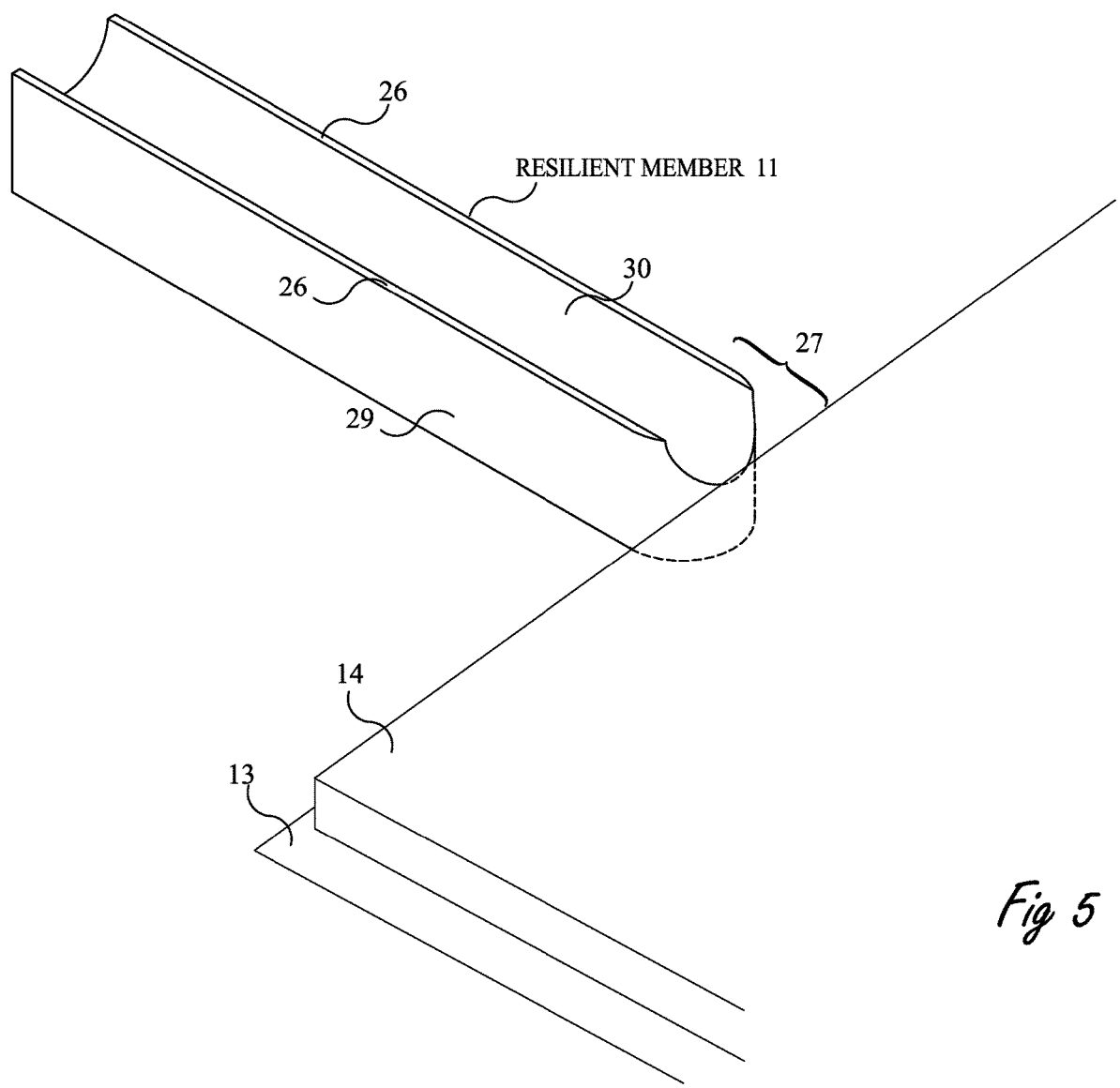
FIG. 5 is another perspective view of the resilient member and table of FIG. 1.

FIGS. 4 and 5 show resilient member 11, which is constructed of highly resilient foam rubber or other suitable viscoelastic compressible cushioning with or without a soft fabric cover (removable or permanent) that may be manufactured through methods well known in the art to safely support and comfortably buttress a multitude of pressure points of extremity 12. Resilient member 11 is a block, rectangular in shape, having a bottom surface 24 that is flat with a longitudinal stripe or band of one half 25 of a hook-and-loop fastener set, a top surface 26 that is flat, a rounded end 27 that is semicircular in shape, a distal end 28, a pair of sides 29, and a furrow 30 that is concave in shape. In addition, furrow 30 is parallel to bottom surface 24, flat top surface 26, and sides 29, and extends longitudinally and centrally from the rounded end 27 to the distal end 28 of the resilient member 11. Also, the distance between bottom surface 24 and the nadir (i.e., the bottom) of furrow 30 is sized so that upper surface of the cushion 14 of the table 13 and nadir of furrow 30 of resilient member 11 nearest table 13 are at approximately the same level. Member 11 is constructed with greater density near its top surface 26 so that this portion is minimally compressible by straps 31 (as shown in FIG. 1 and described in connection with FIGS. 11 and 12) and with lesser density near the nadir of furrow 30 to reduce pressure to pressure points of the extremity 12 (FIG. 1). Board 10 and member 11 are reusable to provide an environmentally conscientious cost-effective device. In other embodiments, board 10 and member 11 can be constructed from recyclable disposal materials, thereby to make the extremity support system cost-effective and environmentally friendly.

Figure 6:
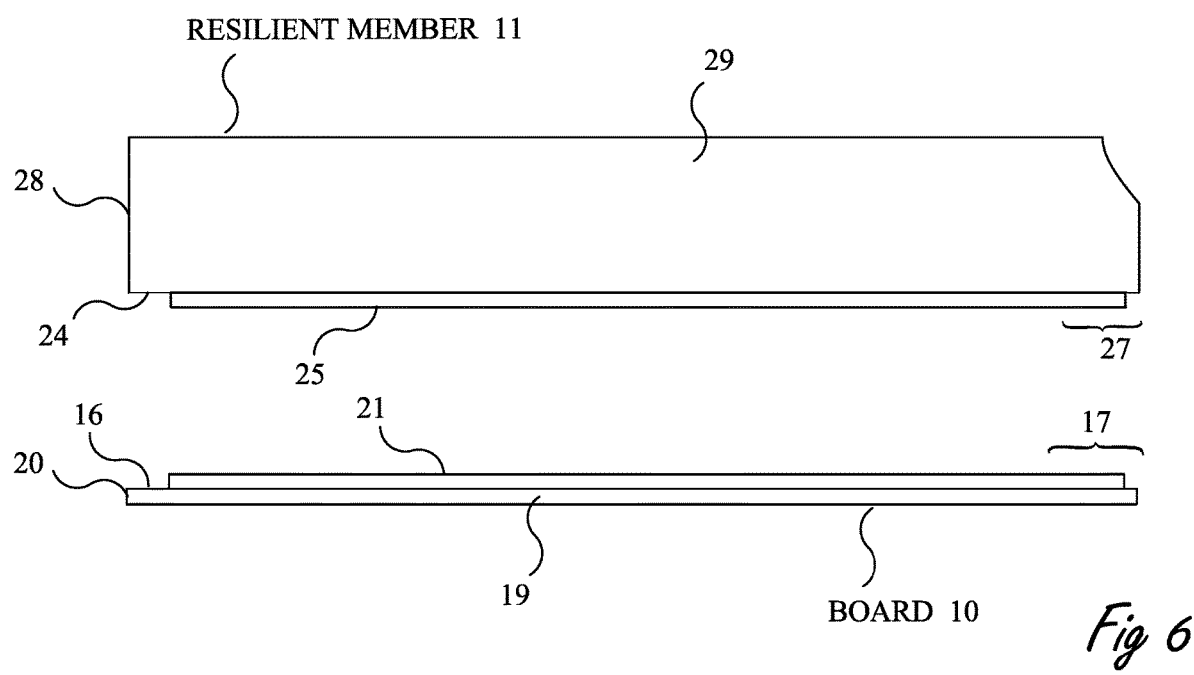
FIG. 6 is a side perspective view of the resilient member and the board (the opposite side being a mirror image) of FIG. 1.
Figure 7:
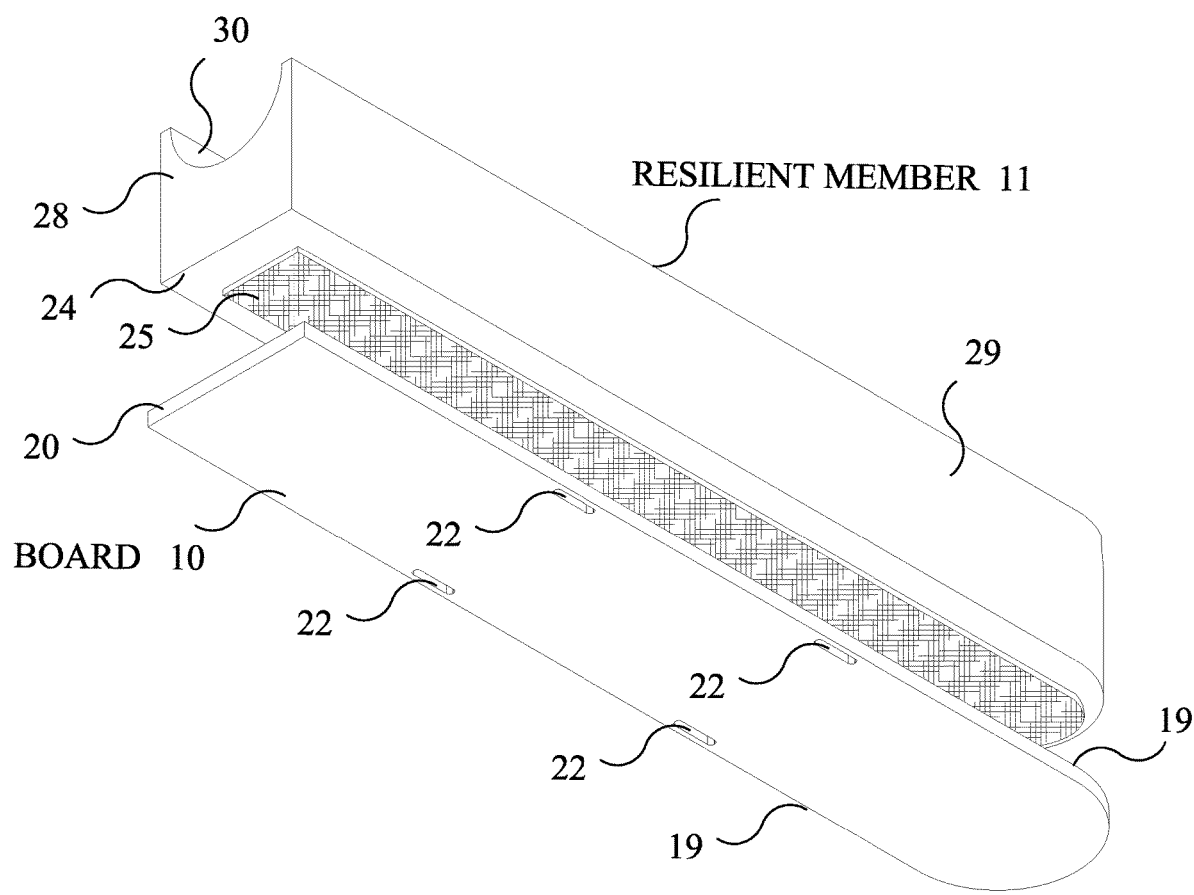
FIG. 7 is another exploded perspective view of the resilient member and the board of FIG. 1.

Operation—First Embodiment—FIGS. 6-8

As shown in FIGS. 6-8, in the first embodiment, board 10 and member 11 are equal in length. In addition, half of the hook-and-loop fastener 21 is attached to upper surface 16 of board 10 which matches the other half of hook-and-loop fastener 25 on bottom 24 of member 11 for removably attaching board 10 to member 11, thereby providing stability for member 11.

When member 11 is attached to board 10, the rounded end 27 of member 11 is placed on top of curved portion 17 of board 10, sides 29 of member 11 are between, parallel, and equidistant from the opposite pair of sides 19 of board 10, and distal end 28 of member 11 and outer end 20 of board 10 are coplanar. This orientation supports and buttresses the pressure points between member 11 and the patient's arm or leg, and provides access to extremity 12 (FIG. 1) placed on furrow 30 of member 11. It also enables board 10 to pivot without hindrances when connected to table 13 and makes the pairs of openings 22 accessible because a plurality of ledge portions on the respective sides 19 of the board 10 are formed that extend out beyond the resilient member 11.

The length of board 10, furrow 30, and the resilient member 11 are greater than the length of a predetermined extremity 12 and has sufficient width, depth, and cross-sectional area to safely support, protect pressure points, and prevent extremity 12 from falling out of furrow 30. Member 11 may be constructed in a plurality of sizes for children, adolescents, small adults, and large adults, or any other suitable categorization of patent sizes.

As described in connection with FIGS. 10-12b, the depth of furrow 30 is designed for placement of straps 31 (as shown in FIG. 1) across the top of resilient member 11 so that straps 31 do not physically touch (i.e., do not engage, do not contact, and do not communicate) extremity 12 in furrow 30. Furrow 30 provides sufficient space and support for extremity 12 to distribute its weight along the concave resting surface of furrow 30, thereby reducing or avoiding pressure points on extremity 12 that can cause injuries. I.e., high pressure is avoided at boney prominences, skin, muscles, lymphatic channels, and neurovascular structures of the extremity 12. Furthermore, member 11 is constructed with lesser density near the nadir of the furrow 30 to provide the least amount of pressure to the vulnerable pressure points of extremity 12. The greater density near top surface 26 of resilient member 11 functions so that straps 31 (as shown in FIG. 1 and in connection with FIGS. 10-12b) minimally compress member 11 and do not touch extremity 12 under usual circumstances.

Figure 9A:
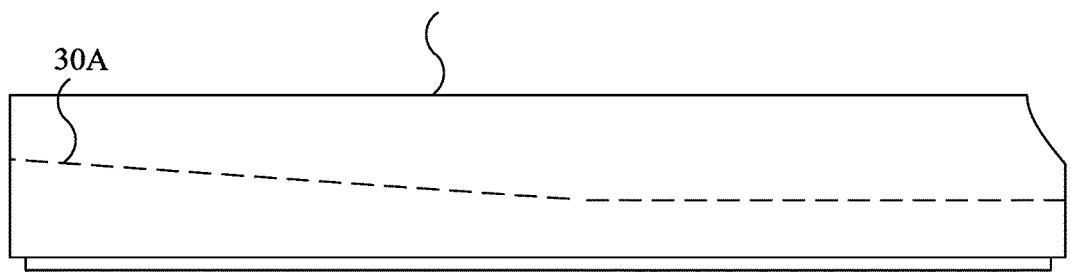
FIG. 9a is a side perspective view of the resilient member of FIG. 1.
Figure 9B:
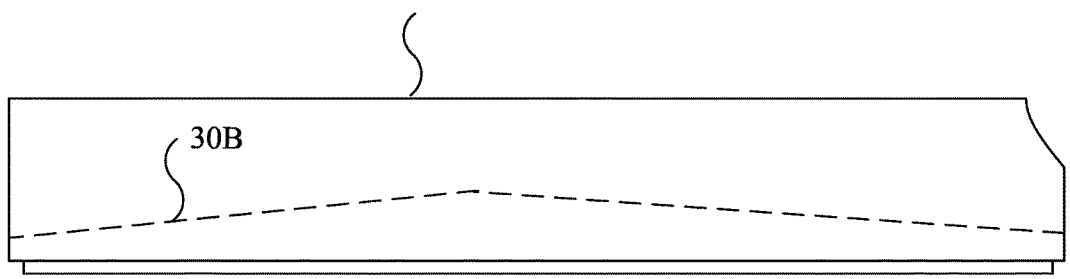
FIG. 9b is another perspective view of the side of the resilient member of FIG. 1.
Figure 10:
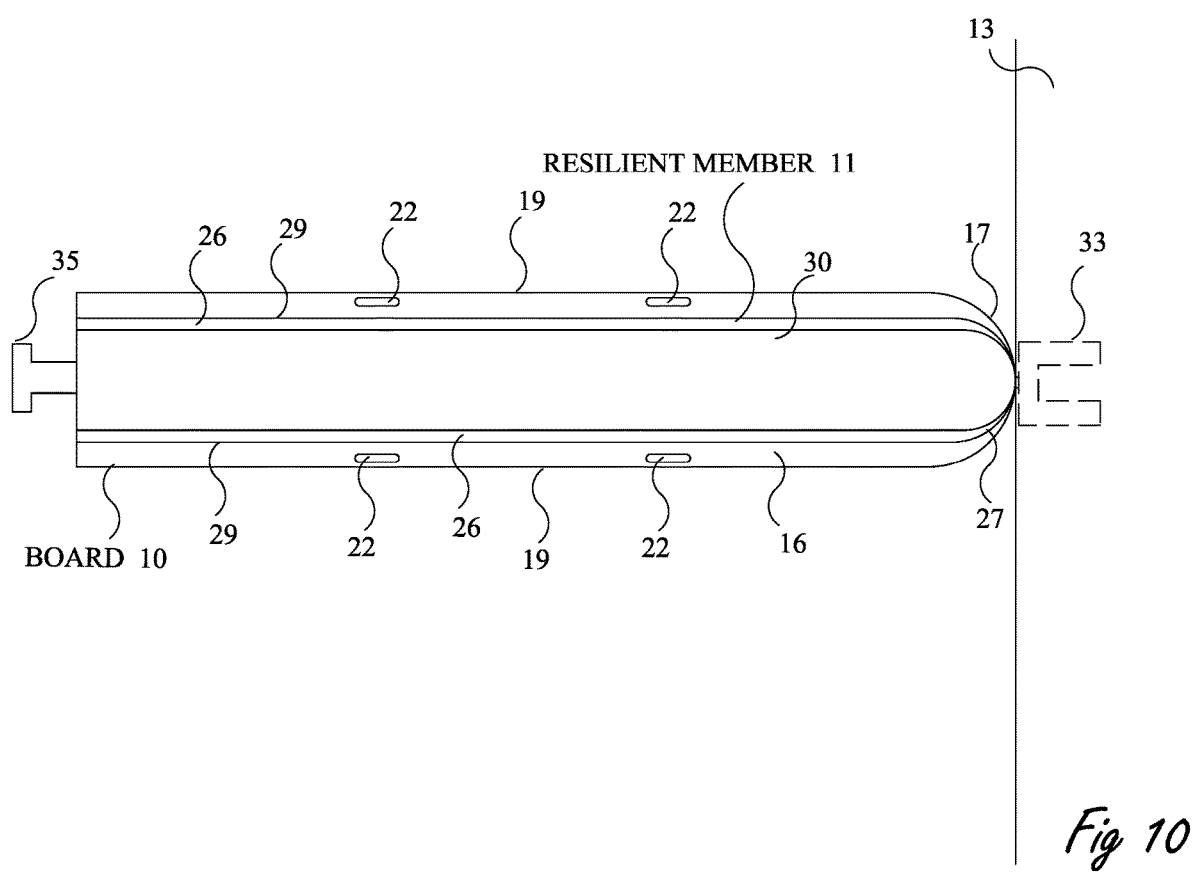
FIG. 10 is a top perspective view of the board and resilient member of FIG. 1.

Description and Operation—Alternative Embodiments—FIGS. 9A-B

The number, size, cross-sectional area, and configuration of matching hook-and-loop fasteners 21, 25 can vary to securely attach board 10 to resilient member 11 in a wide variety of orientations. Also a wide variety of ways to the dimensions, depth, shape, edges, corners, and cross-sectional areas of board 10, furrow 30, and resilient member 11 can be made to support extremity 12 for patients with and without disfigurements, disabilities, and/or special needs in a variety of positions, such as sitting, kneeling, side lying, semi-side lying, lithotomy, jackknife, lateral, prone, and supine and still enable board 10 to pivot. Furthermore, in addition to being level as shown in FIGS. 1 to 8, furrow 30 can also be not level, multi-sloped, and multi-shaped. Furrow 30 can be off-center within the borders of resilient member 11 and provide support and access to the extremity 12. For example, FIGS. 9A and 9B show two alternative embodiments where furrows 30A and 30B are suitable for a bent arm or a bent leg. In FIG. 9A, furrow 30A has a distal inclined portion and a proximal level portion that can be placed closer to table 13 and for supporting a supine patient's arm bent at the elbow or a prone patient's leg bent at the knee. In FIG. 9B, furrow 30B has an anticline surface that can support a supine patient's leg bent at the knee or a prone patient's arm bent at the elbow. Furrows 30 of various other sizes and shapes are especially advantageous for patients with disfigurements, disabilities, and special needs having arms and legs of various sizes and shapes.

Operation—Alternative Embodiment—FIGS. 10-12B

FIGS. 10-12B show openings 22 and a preferred placement of a plurality of guardrail straps 31, which have hook-and-loop fasteners. The straps 31 are partly shown in FIGS. 11-12B and their paths are similar on each side 19 of the board 10 and resilient member 11. Each strap 31 has paths and sufficient length to pass through openings 22, extend around resilient member 11 in two layers, and allow a pair of strap ends 32 of strap 31 attach together. I.e., one strap end 32 is threaded from upper surface 16 to undersurface 15 through one opening 22 on one side 19 of board 10 and the other strap end 32 is threaded from upper surface 16 to undersurface 15 through one opening 22 on the opposite side 19 of board 10. Then, strap 31 is doubled over itself so that the ends 32 of each strap 31 overlap to attach together over furrow 30. Straps 31 are perpendicular to the longitudinal axis of furrow 30 with both layers extending over furrow 30. Straps 31 do not touch extremity 12 (FIG. 1) because they extend over the top of member 11 and furrow 30 is deeper than the lateral height of the extremity 12. Straps 31 enable access to extremity 12 and function with furrow 30 to prevent extremity 12 from being removed from member 11. Each pair of openings 22 is accessible and located near each of the opposite pair of sides 19 of board 10 for holding straps 31.

Each strap 31 of hook-and-loop fasteners is oriented with its loops (i.e., the softer part of the hook-and loop fasteners), facing extremity 12. Analogous to the function and purpose of a highway guardrail, each strap 31 prevents the risk of a serious accident by serving as a barrier, sentry, barricade, blockade, guardian, and gatekeeper to prevent extremity 12 being inadvertently removed from furrow 30. Furthermore, guardrail straps 31 are non-occlusive and non-obstructive because they do not bind, grip, grasp, hold, and/or immobilize extremity 12 and do not occlude a multitude of intravascular lines and vascular and lymphatic spaces (e.g., arteries, veins, lymphatic channels, dialysis fistulas); and do not create occlusion that can damage the extremity 12, including but not limited to, its neurovascular structures, soft tissues, joints, musculoskeletal structures, and skin. Straps 31 enable movable adjustments of extremity 12 without interfering with the function of a multitude of medical devices placed in and on extremity 12 and the device 23 which pivotally attaches board 10 to the table 13.

Operation—Alternative Embodiments—FIGS. 10-12b

In other embodiments, resilient member 11 is constructed with a plurality of degrees of compressibility to minimize pressure at the multitude of pressure points of extremity 12 without and with disabilities, disfigurements, and special needs, whereby guardrail straps 31 do not touch extremity 12 under usual circumstances. For example, the regions of furrow 30 that contact an elbow or a heel can be constructed to be more compressible to reduce pressure points that could be particularly beneficial in a compromised patient with a pressure ulcer of their elbow and/or heel. Guardrail straps 31 can be positioned at angles other than 90° to furrow 30 so that the straps 31 intersect and yet still do not touch extremity 12 or attachment device 23 to accommodate patients without and with disabilities, disfigurements, and special needs, such as patients with fractured or disfigured extremities from strokes, cerebral palsy, traumatic injuries, neuromuscular disorders, and/or degenerative joint diseases, and for patients where minimizing pressure points to their extremity 12 is essential, such as in post-surgical breast cancer patients and patients with fistulas in their arms used for hemodialysis. In other embodiments, straps 31 and openings 22 can have alternative configurations and sizes.

In other embodiments, member 11 may or may not cover openings 22 and straps 31 can be attached. For example, before attaching member 11 to board 10, each strap 31 can be threaded through openings 22 so that each strap extends to each of opposite sides 19 and rest on upper surface 16 of board 10. Member 11 is then attached to board 10, followed by attaching strap ends 32 to each other over member 11.

In other embodiments, the number, location, dimensions, cross-sectional area, and spacing of each opening 22 can vary to engage a plurality of various types of guardrail straps 31. In other embodiments, straps 31 can pass through openings 22 from undersurface 15 to upper surface 16 of board 10, loop through openings 22, and intersect or not intersect to provide additional support to member 11 and still avoid physical contact with extremity 12 and attachment device 23. In other embodiments, strap ends 32 can overlap and attach together over one or the other opposite sides 29 of resilient member 11. Furthermore, straps 31 can be placed and repositioned with extremity 12 in furrow 10 without traumatizing extremity 12 or hindering pivoting of board 10 and provide additional stability to member 11. In other embodiments, straps 31 can be attached to openings 22 using other hardware such as hooks and clamps. In other embodiments, the openings 22 can also function to help maneuver the board 10 when it is being positioned and/or openings 22 can hold a multitude of medical instruments and containers.

Figure 13:
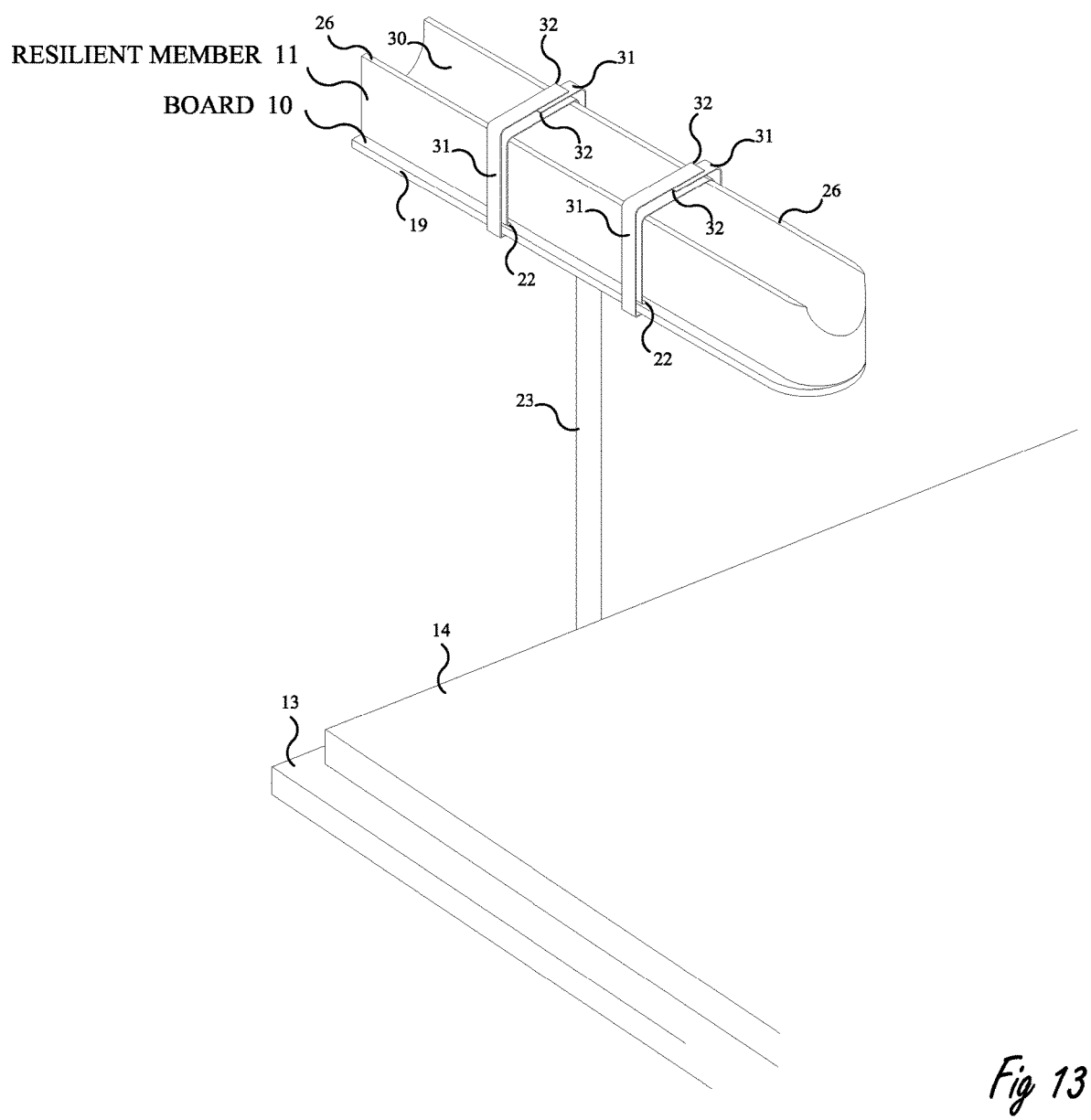
FIG. 13 is another perspective view the resilient member, including straps, attached to a board connected to a table of FIG. 1.

Operation—Alternative Embodiments—FIG. 13

In other embodiments, a plurality of pivoting attachment devices 23 known to those skilled in the art can fasten to undersurface 15 of board 10 to attach the board to table 13 to position the board 10, resilient member 11, and straps 31 in a plurality of planes and at a multitude of levels and distances at, below, or above table 13. As exemplified in FIG. 13, the extremity support system can be positioned above the surface of table 13 to support the arm of the patient placed in a lateral position on table 13 for procedures such as adrenal and kidney surgery or to support the leg of the patient in a lithotomy position for genital procedures. In addition, patients in a jackknife or a prone position, for example, can benefit from placing their arm or leg on the extremity support system positioned below the surface of table 13. In other embodiments, the extremity support system placed at the level of table 13 can be positioned a plurality of distances away from table 13 to enhance pivoting of the system for supporting extremities 12 of various patients with and without disabilities, disfigurements, and special needs. The system accommodates the common practice of pivoting board 10 and supporting extremity 12 extending off the supporting surface of table 13 for a plurality of patient positions, such as sitting, kneeling, side lying, semi-side lying, lithotomy, jackknife, lateral, prone, and supine.

CONCLUSIONS, RAMIFICATIONS, AND SCOPE

Accordingly, the reader will see that, according to one or more aspects, I have provided one device that has the following advantages, that include, but are not limited to the following:

1. The extremity support system is designed to be used to support either the right or the left arm or leg of patients (human or animal), thereby cost-effectively replacing a multitude of other devices that support only the arm or the leg.

2. The components of the system can be constructed from recyclable disposal or reusable materials thereby being a cost-effective and environmentally responsible device.

3. Board 10 is constructed from rigid radiolucent or radiopaque hard materials that can support resilient member 11 constructed of highly resilient foam rubber or other suitable viscoelastic cushioning with or without a soft fabric cover (removable or permanent). Furrow 30 supports extremity 12 comfortably, ergonomically, securely, and safely, and also provides access to, and softly buttresses the many pressure points of extremity 12 that extend off the surface of the table 13 when stationary and during moveable adjustments of table 13, the patient, extremity 12, resilient member 11, and extremity support system.

4. Board 10 and resilient member 11 attach together by matching halves of hook-and-loop fasteners 21, 25 that stabilize the resilient member 11.

5. Board 10 can attach to any side or end of table 13 using well known devices so that the system can lock in position, move, or pivot without hindrances and support extremity 12 ergonomically, comfortably, and safely in a multitude of patient positions, such as sitting, kneeling, side lying, semi-side lying, lithotomy, jackknife, lateral, prone, and supine.

6. Board 10 has openings 22 for engaging straps 31, whereby the straps 31 do not communicate or interfere with attachment device 23 fastened to the undersurface of board 10.

7. The system is designed so that straps 31 can be placed in a plurality of configurations that will remain in position. Under usual circumstances, straps 31 do not have physical contact with extremity 12 to avoid pressure points, occlusion, obstruction and/or trauma. Straps 31 can physically contact extremity 12 when it is lifted to the level of strap 31 to safely prevent inadvertent removal of extremity 12 from furrow 30, and therefore provides additional advantages over restraints as described in prior art devices.

8. Straps 31 do not obstruct, occlude, and/or interfere with the proper function of the intravascular lines, vascular structures, and lymphatic channels of extremity 12 and/or the multitude of medical devices placed into and onto extremity 12, and prevent any damage to the extremity 12 such as its neurovascular structures, soft tissues, joints, musculoskeletal structures, and skin.

9. The system allows openings 22 to engage a plurality of straps 31 in a plurality of configurations to provide additional stability to the resilient member 11.

10. The system safely and comfortably supports extremity 12, prevents it from falling out of furrow 30 and off resilient member 11, enables movable non-traumatic, non-occlusive, non-obstructive adjustments of extremity 12 during repositioning of extremity 12, the patient, table 13, resilient member 11, or extremity support system.

While the above description contains many specificities, these should not be construed as limitations on the scope, but as exemplifications of some present embodiments. Many other ramifications and variations are possible within the teachings. For example, board 10 can be adapted for use to support extremity 12 without resilient member 11 or for use with other types of extremity support devices mounted on top of board 10, wherein straps 31 may or may not be used. Also, resilient member 11 can be adapted for use to support extremity 12 on top of a surface without board 10 with or without the use of straps 31. Use of resilient member 11 is not limited to surgical procedures and can be used to support the arms and legs on board 10 attached to various types of patient supports, such as hospital or ordinary beds, and massage, chiropractic, or acupuncture tables, where a user is placed in a multitude of positions. The terms "operating table, treatment table, and bed" as used in the description should be understood to mean any type of patient support, such as a surgical table, treatment table, chair, stretcher, backboard, or bed. For example, resilient member 11 and/or board 10 may be attached to a backboard used to rescue and transport an injured patient to prevent further bodily harm. Furthermore, member 11 can be used to support an extremity 12 of a non-human animal as can be used by those skilled in the art of veterinary medicine. It may be used (or easily adapted for use) with a multitude of types of patients having a multitude of types of surgeries and non-surgical treatments in a plurality of positions on an operating table, treatment table, or bed.

The invention claimed is:

1. A support for a patient's extremity that extends off the surface of a table or bed, comprising:
    a board having an upper surface, an undersurface surface, a curved portion, a platform portion, an outer end, a pair of sides, and a plurality of strap openings adjacent to said respective sides, each said opening having a predetermined shape;
    a resilient member comprising a compressible elongated block having a top surface, a bottom surface, a rounded end, a distal end, and a longitudinal top furrow which extends from said rounded end to said distal end, said resilient member and said furrow having a predetermined shape and size for supporting a patient's extremity within a predetermined range of sizes;
    wherein said rounded end of said resilient member overlies and is coincident with said curved portion of said board and said distal end of said resilient member overlies and is coincident with said outer end of said board;
    wherein said resilient member is narrower than said board so as to have a plurality of ledge portions on said respective sides of said board that extend out from said board, said plurality of openings being formed in said ledge portions;
    and a strap that extends through said openings of said board and spans over said furrow of said resilient member;
    whereby said extremity support provides comfortable, safe, ergonomic support, and buttresses pressure points of said extremity, and yet allows access to said extremity, enables moveable non-traumatic adjustments of said extremity in said furrow, and prevents accidental removal of said extremity from said resilient member.

2. The extremity support of claim 1 wherein said board comprises rigid hard material having radiolucent and/or radiopaque features.

3. The extremity support of claim 1, further including an attachment device for attaching said board to a side or end of said table or bed.

4. The extremity support of claim 3 wherein said attachment device is arranged to pivot said board about said table or bed and enable said extremity support to be moved to and locked into a plurality of positions.

5. The extremity support of claim 1 wherein said upper surface of said board and said bottom surface of said resilient member have respective mating hook-and-loop fasteners attached thereto for removably attaching said board and said resilient member together.

6. The extremity support of claim 1 wherein said strap is free from said bottom surface of said board between said openings so that said strap does not interfere with the function of said attachment device.

7. The extremity support of claim 1 wherein said furrow of said resilient member is of sufficient cross-sectional area to enable movable adjustments of and provide access to said extremity for placement, removal, troubleshooting, and maintenance of a plurality of medical devices placed in or on said extremity.

8. The extremity support of claim 1 wherein said furrow of said resilient member has sufficient cross-sectional area and depth so that said strap can span over said furrow without contacting said extremity.

9. The extremity support of claim 1 wherein said strap is arranged to span over said furrow in a plurality of layers so that said strap can function as a guardrail that prevents removal of said extremity from said furrow.

10. The extremity support of claim 1 wherein said strap is of sufficient length to extend from one end above said furrow, down past one side of said resilient member and one outer side of said board, under said outer side of said board, up through one of said strap openings, up past said one side of said resilient member to said top of said resilient member, across top opening of said furrow, down one opposite side of said resilient member and through an opposite strap opening, under one opposite side of said board, up past said opposite side of said resilient member to said top of said resilient member, and above said furrow to overlap and removably attach to an opposite end of said strap, so that said strap can function as a guardrail that prevents removal of said extremity from said furrow.

11. The extremity support of claim 1 wherein said strap has end portions having mating hook-and-loop attachment areas for holding said ends together.

12. The extremity support of claim 1 wherein a second strap having hook-and-loop fasteners and a second plurality of openings are provided, said second strap being spaced from said first-named strap and extending through said second plurality of openings, said second strap and said second plurality of openings being spaced from said first-named strap and said first-named plurality of openings, said second strap spanning over said furrow of said resilient member, said resilient member, said board, and said straps being selected from the class consisting of disposable and reusable materials.

13. A method of supporting a patient's extremity, where the patient is on a table or a bed and said extremity extends out from the surface of said table or bed, comprising:

providing a board having an upper surface, an undersurface, a curved portion, a platform portion, an outer end, a pair of sides, and a pair of strap openings adjacent to said respective sides, each said opening having a predetermined shape;

providing a resilient member comprising a compressible elongated block having a top surface, a bottom surface, a rounded end, a distal end, and a longitudinal top furrow which extends from said rounded end to said distal end, said resilient member and said furrow having a predetermined shape and size for supporting said patient's extremity within a predetermined range of sizes; and providing a strap that can extend through said openings of said board and span over said furrow of said resilient member;

placing said patient on said bed or table and putting said extremity of said patient into said furrow and attaching said strap so that it extends through said openings of said board and spans over said furrow above and not communicating with said extremity, whereby said extremity support provides comfortable, safe, ergonomic support, and buttresses pressure points of said extremity, and yet allows access to said extremity, enables moveable non-23 traumatic adjustments of said extremity in said furrow, and prevents accidental removal of said extremity from said resilient member;

wherein said strap extends from one end above said furrow, down past one side of said resilient member and one outer side of said board, under said outer side of said board, up through one of said strap openings, up past said one side of said resilient member to said top of said resilient member, across top opening of said furrow, down one opposite side of said resilient member and through a strap opening on an opposite side of said board, under said opposite side of said board, up past said opposite side of said board and said resilient member to said top of said resilient member, and above said furrow to an opposite end of said strap and is removably attached to said opposite end of said strap, so that said strap can function as a guardrail that prevents removal of said extremity from said furrow.

14. The method of claim 13, further including providing an attachment device for attaching said board to a side or end of said table or bed.

15. The method of claim 14 wherein said attachment device is arranged to pivot said board about said table or bed and enables said extremity support to be moved to and locked into a plurality of positions.

16. The method claim 13 wherein said strap is arranged to span over said furrow in a plurality of layers so that said strap can function as a guardrail that prevents removal of said extremity from said furrow.

17. The method of claim 13, further including a second strap having hook-and-loop fasteners and a second plurality of openings, said second strap being spaced from said first-named strap and extending through said second plurality of openings, said second strap and said second plurality of openings being spaced from said first-named strap and said first-named plurality of openings, said second strap spanning over said furrow of said resilient member, said resilient member, said board, so that said straps each extend through said openings at opposite sides of said board and loop around said sides of said board outside of said openings and form two layers on said sides and above said resilient member.

* * * * *